(12) United States Patent
Nalagatla et al.

(10) Patent No.: US 12,023,032 B2
(45) Date of Patent: *Jul. 2, 2024

(54) ANVIL FOR CIRCULAR SURGICAL STAPLER AND ASSOCIATED METHOD OF MANUFACTURE WITH MIM

(71) Applicant: Cilag GmbH International, Zug (CH)

(72) Inventors: Anil K. Nalagatla, Mason, OH (US); Frederick E. Shelton, IV, Hillsboro, OH (US); Chester O. Baxter, III, Loveland, OH (US); Amit Gupta, Pune (IN); Sambit Kumar Acharya, Kolkata (IN)

(73) Assignee: Cilag GmbH International, Zug (CH)

( * ) Notice: Subject to any disclaimer, the term of this patent is extended or adjusted under 35 U.S.C. 154(b) by 103 days.

This patent is subject to a terminal disclaimer.

(21) Appl. No.: 17/155,799

(22) Filed: Jan. 22, 2021

(65) Prior Publication Data

US 2021/0196278 A1 Jul. 1, 2021

Related U.S. Application Data

(63) Continuation of application No. 16/236,700, filed on Dec. 31, 2018, now Pat. No. 11,291,450.

(51) Int. Cl.
*A61B 17/115* (2006.01)
*B21K 5/00* (2006.01)
*A61B 17/00* (2006.01)

(52) U.S. Cl.
CPC ............ *A61B 17/1155* (2013.01); *B21K 5/00* (2013.01); *A61B 2017/00477* (2013.01); *A61B 2017/00526* (2013.01); *A61B 2017/00734* (2013.01)

(58) Field of Classification Search
CPC ...... A61B 17/1155; A61B 2017/00477; A61B 2017/00526; A61B 2017/00734;
(Continued)

(56) References Cited

U.S. PATENT DOCUMENTS

| 4,119,258 A | 10/1978 | Ewig, Jr. |
| 4,184,620 A | 1/1980 | Ewig |

(Continued)

FOREIGN PATENT DOCUMENTS

| CN | 104107078 A | 10/2014 | |
| EP | 2928388 B1 * | 1/2019 | ......... A61B 17/1155 |

(Continued)

OTHER PUBLICATIONS

European Search Report, Partial, and Provisional Written Opinion dated Apr. 29, 2020, for Application No. 19219993.3, 11 pages.

(Continued)

*Primary Examiner* — Robert F Long
(74) *Attorney, Agent, or Firm* — Frost Brown Todd LLP

(57) ABSTRACT

A method is used to manufacture an anvil of a surgical circular stapler. The anvil includes a head and a shank extending proximally from the head. The method includes forming the head of a surgical circular stapler using a metal injection molding process. The method also includes forming an annular array of staple forming pockets in the head. The method also includes machining the shank of the surgical circular stapler. The method also includes coupling together the head and the shank of the surgical circular stapler that were separately manufactured.

20 Claims, 13 Drawing Sheets

(58) Field of Classification Search
CPC .......... A61B 2017/07257; A61B 2017/07264; B21K 5/00
USPC .......................................... 227/175.1–182.1
See application file for complete search history.

(56) References Cited

U.S. PATENT DOCUMENTS

| | | | |
|---|---|---|---|
| 4,224,267 A | 9/1980 | Lugosi et al. | |
| 4,706,866 A | 11/1987 | Ebihara | |
| 4,813,143 A | 3/1989 | Scheminger et al. | |
| 5,104,025 A * | 4/1992 | Main | A61B 17/115 227/19 |
| 5,163,945 A | 11/1992 | Ortiz et al. | |
| 5,205,459 A * | 4/1993 | Brinkerhoff | A61B 17/115 227/19 |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,297,746 A | 3/1994 | McBride et al. | |
| 5,308,576 A | 5/1994 | Green et al. | |
| 5,312,024 A * | 5/1994 | Grant | A61B 17/115 227/19 |
| 5,333,773 A | 8/1994 | Main et al. | |
| 5,342,373 A | 8/1994 | Stefanchik et al. | |
| 5,350,104 A | 9/1994 | Main et al. | |
| 5,364,001 A | 11/1994 | Bryan | |
| 5,392,979 A * | 2/1995 | Green | A61B 17/115 227/19 |
| 5,403,312 A | 4/1995 | Yates et al. | |
| 5,409,276 A | 4/1995 | Engasser | |
| 5,411,514 A * | 5/1995 | Fucci | A61B 17/32002 606/180 |
| 5,431,668 A | 7/1995 | Burbank, III et al. | |
| 5,445,167 A | 8/1995 | Yoon et al. | |
| 5,480,089 A * | 1/1996 | Blewett | A61B 17/072 227/19 |
| 5,487,499 A | 1/1996 | Sorrentino et al. | |
| 5,533,661 A | 7/1996 | Main et al. | |
| 5,584,845 A | 12/1996 | Hart | |
| 5,601,573 A | 2/1997 | Fogelberg et al. | |
| 5,722,306 A | 3/1998 | Vela et al. | |
| 5,807,338 A | 9/1998 | Smith et al. | |
| 5,951,574 A | 9/1999 | Stefanchik et al. | |
| 6,142,933 A * | 11/2000 | Longo | A61B 1/31 600/184 |
| 6,176,021 B1 | 1/2001 | Sato et al. | |
| 6,185,771 B1 | 2/2001 | Trusty, Sr. | |
| 6,269,714 B1 | 8/2001 | Sakai | |
| 6,959,851 B2 | 11/2005 | Heinrich | |
| 6,988,650 B2 | 1/2006 | Schwemberger et al. | |
| 7,000,818 B2 | 2/2006 | Shelton, IV et al. | |
| 7,043,819 B1 | 5/2006 | Arnold | |
| 7,134,587 B2 | 11/2006 | Schwemberger et al. | |
| 7,147,140 B2 | 12/2006 | Wukusick et al. | |
| 7,195,631 B2 | 3/2007 | Dumbauld | |
| 7,204,404 B2 | 4/2007 | Nguyen et al. | |
| 7,207,472 B2 | 4/2007 | Wukusick et al. | |
| 7,261,724 B2 | 8/2007 | Molitor et al. | |
| 7,380,696 B2 | 6/2008 | Shelton, IV et al. | |
| 7,422,139 B2 | 9/2008 | Shelton, IV et al. | |
| 7,464,849 B2 | 12/2008 | Shelton, IV et al. | |
| 7,670,334 B2 | 3/2010 | Hueil et al. | |
| 7,686,820 B2 | 3/2010 | Huitema et al. | |
| 7,699,860 B2 | 4/2010 | Huitema et al. | |
| 7,731,724 B2 | 6/2010 | Huitema et al. | |
| 7,753,245 B2 | 7/2010 | Boudreaux et al. | |
| 7,771,425 B2 | 8/2010 | Dycus et al. | |
| 7,845,537 B2 | 12/2010 | Shelton, IV et al. | |
| 7,918,377 B2 * | 4/2011 | Measamer | A61B 17/1155 227/176.1 |
| 7,975,895 B2 * | 7/2011 | Milliman | A61B 17/1155 227/19 |
| 7,980,443 B2 | 7/2011 | Scheib et al. | |
| 8,008,598 B2 * | 8/2011 | Whitman | B23K 26/361 219/121.69 |
| 8,021,389 B2 | 9/2011 | Molz | |
| 8,038,686 B2 | 10/2011 | Huitema et al. | |
| 8,087,562 B1 | 1/2012 | Manoux et al. | |
| 8,118,206 B2 * | 2/2012 | Zand | A61B 5/0086 227/176.1 |
| 8,210,411 B2 | 7/2012 | Yates et al. | |
| 8,220,688 B2 | 7/2012 | Laurent et al. | |
| 8,262,679 B2 | 9/2012 | Nguyen | |
| 8,308,040 B2 | 11/2012 | Huang et al. | |
| 8,393,514 B2 | 3/2013 | Shelton, IV et al. | |
| 8,408,439 B2 | 4/2013 | Huang et al. | |
| 8,453,914 B2 | 6/2013 | Laurent et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 8,770,458 B2 * | 7/2014 | Scirica | A61B 17/07207 227/176.1 |
| 8,910,847 B2 | 12/2014 | Nalagatla et al. | |
| 9,072,535 B2 | 7/2015 | Shelton, IV et al. | |
| 9,101,358 B2 | 8/2015 | Kerr et al. | |
| 9,186,142 B2 | 11/2015 | Fanelli et al. | |
| 9,192,383 B2 | 11/2015 | Milliman | |
| 9,345,481 B2 | 5/2016 | Hall et al. | |
| 9,517,065 B2 | 12/2016 | Simms et al. | |
| 9,713,469 B2 | 7/2017 | Leimbach et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,867,615 B2 | 1/2018 | Fanelli et al. | |
| 9,907,552 B2 | 3/2018 | Measamer et al. | |
| 9,936,949 B2 | 4/2018 | Measamer et al. | |
| 10,092,292 B2 | 10/2018 | Boudreaux et al. | |
| 10,687,814 B2 | 6/2020 | Dunki-Jacobs et al. | |
| 11,266,405 B2 * | 3/2022 | Shelton, IV | B23K 26/21 |
| 2005/0004568 A1 | 1/2005 | Lawes et al. | |
| 2005/0139636 A1 | 6/2005 | Schwemberger et al. | |
| 2005/0143759 A1 | 6/2005 | Kelly | |
| 2005/0145672 A1 | 7/2005 | Schwemberger et al. | |
| 2005/0149087 A1 | 7/2005 | Ahlberg et al. | |
| 2005/0187576 A1 * | 8/2005 | Whitman | A61B 17/1155 227/176.1 |
| 2006/0047309 A1 | 3/2006 | Cichocki | |
| 2006/0090603 A1 | 5/2006 | Lewis et al. | |
| 2006/0108393 A1 * | 5/2006 | Heinrich | A61B 17/00491 227/179.1 |
| 2006/0135992 A1 * | 6/2006 | Bettuchi | A61B 17/115 606/219 |
| 2006/0219752 A1 | 10/2006 | Arad et al. | |
| 2007/0056932 A1 * | 3/2007 | Whitman | B23K 26/361 219/68 |
| 2007/0169605 A1 | 7/2007 | Szymanski | |
| 2007/0175955 A1 | 8/2007 | Shelton, IV et al. | |
| 2008/0078800 A1 | 4/2008 | Hess et al. | |
| 2008/0142187 A1 | 6/2008 | Jadeed et al. | |
| 2008/0243106 A1 * | 10/2008 | Coe | A61B 17/00234 606/1 |
| 2008/0269793 A1 * | 10/2008 | Scirica | A61B 17/07207 606/190 |
| 2008/0308605 A1 | 12/2008 | Scirca | |
| 2009/0001128 A1 | 1/2009 | Weisenburgh, II et al. | |
| 2010/0094315 A1 * | 4/2010 | Beardsley | A61B 17/07207 606/143 |
| 2010/0127039 A1 | 5/2010 | Hessler | |
| 2010/0249807 A1 | 9/2010 | Chen et al. | |
| 2011/0042440 A1 * | 2/2011 | Holsten | A61B 17/1155 227/176.1 |
| 2011/0068147 A1 | 3/2011 | Racenet et al. | |
| 2011/0095067 A1 * | 4/2011 | Ohdaira | A61B 17/07207 606/49 |
| 2012/0116422 A1 | 5/2012 | Triplett et al. | |
| 2012/0143218 A1 * | 6/2012 | Beardsley | A61B 17/00234 606/142 |
| 2012/0234890 A1 * | 9/2012 | Aronhalt | A61B 17/07207 227/175.1 |
| 2012/0292366 A1 | 11/2012 | Nalagatla et al. | |

(56) References Cited

U.S. PATENT DOCUMENTS

| | | |
|---|---|---|
| 2012/0292371 A1 | 11/2012 | Nalagatla et al. |
| 2012/0292372 A1* | 11/2012 | Nalagatla ......... A61B 17/07292 227/179.1 |
| 2013/0105548 A1* | 5/2013 | Hodgkinson .... A61B 17/07292 227/176.1 |
| 2013/0214027 A1* | 8/2013 | Hessler ................ A61B 17/068 227/175.1 |
| 2013/0256382 A1 | 10/2013 | Swayze et al. |
| 2014/0191012 A1* | 7/2014 | Chen .................... A61B 17/115 227/176.1 |
| 2014/0197224 A1* | 7/2014 | Penna ................. A61B 17/115 227/179.1 |
| 2014/0239037 A1* | 8/2014 | Boudreaux ...... A61B 17/07207 227/175.1 |
| 2014/0263552 A1 | 9/2014 | Hall et al. |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2016/0374672 A1 | 12/2016 | Bear et al. |
| 2017/0027571 A1 | 2/2017 | Nalagatla et al. |
| 2017/0258471 A1 | 9/2017 | DiNardo et al. |
| 2017/0265867 A1 | 9/2017 | Nativ et al. |
| 2017/0281188 A1* | 10/2017 | Shelton, IV ......... A61B 17/105 |
| 2018/0056095 A1 | 3/2018 | Messerly et al. |
| 2018/0085932 A1 | 3/2018 | Chen |
| 2018/0116667 A1* | 5/2018 | Bae .................... A61B 17/1155 |
| 2018/0132849 A1 | 5/2018 | Miller et al. |
| 2018/0132853 A1 | 5/2018 | Miller et al. |
| 2018/0168647 A1* | 6/2018 | Shelton, IV ....... A61B 17/0644 |
| 2018/0310938 A1 | 11/2018 | Kluener et al. |
| 2018/0310939 A1 | 11/2018 | Stager et al. |
| 2018/0325502 A1* | 11/2018 | Swader .............. A61B 17/3421 |
| 2018/0368839 A1 | 12/2018 | Shelton, IV et al. |
| 2018/0368840 A1 | 12/2018 | Shelton, IV et al. |
| 2018/0368841 A1* | 12/2018 | Shelton, IV ..... A61B 17/07207 |
| 2018/0368842 A1 | 12/2018 | Shelton, IV et al. |
| 2018/0368843 A1 | 12/2018 | Shelton, IV et al. |
| 2019/0000481 A1* | 1/2019 | Harris .............. A61B 17/07292 |
| 2019/0046193 A1 | 2/2019 | Dunki-Jacobs et al. |
| 2019/0090875 A1* | 3/2019 | Fox .................... A61B 17/1155 |
| 2019/0118352 A1* | 4/2019 | Weber ........................ B25F 5/02 |
| 2019/0216561 A1 | 7/2019 | Manzo et al. |
| 2019/0254679 A1 | 8/2019 | Russell |
| 2019/0298374 A1* | 10/2019 | Guerrera ............ A61B 17/1155 |
| 2019/0341753 A1 | 11/2019 | Nemoto et al. |
| 2020/0054322 A1 | 2/2020 | Harris et al. |
| 2020/0054323 A1 | 2/2020 | Harris et al. |
| 2020/0205815 A1 | 7/2020 | Nalagatla et al. |
| 2020/0205816 A1* | 7/2020 | Nalagatla ............. A61B 17/072 |
| 2020/0205835 A1 | 7/2020 | Nalagatla et al. |
| 2020/0206805 A1 | 7/2020 | Nalagatla et al. |
| 2020/0237368 A1* | 7/2020 | Bruns ................ A61B 17/0684 |
| 2020/0237370 A1* | 7/2020 | Fanelli ............ A61B 17/07207 |
| 2021/0161526 A1* | 6/2021 | Srinivas ........... A61B 17/07207 |
| 2021/0177401 A1* | 6/2021 | Abramek ........... A61B 17/0684 |
| 2023/0117309 A1* | 4/2023 | Nalagatla ........... A61B 17/1155 227/179.1 |

FOREIGN PATENT DOCUMENTS

| | | | |
|---|---|---|---|
| EP | 3613358 A1 * | 2/2020 | ........... A61B 17/072 |
| ES | 2611957 T3 * | 5/2017 | ......... A61B 17/1155 |
| WO | WO 2016/179737 A1 | 11/2016 | |
| WO | WO 2017/197594 A1 | 11/2017 | |

OTHER PUBLICATIONS

European Search Report, Extended, and Written Opinion dated Aug. 7, 2020, for Application No. 19219993.3, 12 pages.

International Search Report and Written Opinion dated Jun. 23, 2020, for Application No. PCT/IB2019/060822, 17 pages.

Brazilian Examination Report dated Jul. 5, 2023 for Application No. BR 112021012566-3, 4 pgs.

Indian Examination Report dated Jan. 19, 2023 for Application No. IN 202117027714, 3 pgs.

\* cited by examiner

US 12,023,032 B2

ANVIL FOR CIRCULAR SURGICAL STAPLER AND ASSOCIATED METHOD OF MANUFACTURE WITH MIM

This application is a continuation of U.S. patent application Ser. No. 16/236,700, entitled "Anvil for Circular Surgical Stapler and Associated Method of Manufacture with MIM," filed Dec. 31, 2018, issued as U.S. Pat. No. 11,291,450 on Apr. 5, 2022.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, now U.S. Pat. No. 9,936,949, issued Apr. 10, 2018; U.S. Pub. No. 2015/0083774, entitled "Control Features for Motorized Surgical Stapling Instrument," published Mar. 26, 2015, now U.S. Pat. No. 9,907,552, issued Mar. 6, 2018; and U.S. Pub. No. 2015/0083775, entitled "Surgical Stapler with Rotary Cam Drive," published Mar. 26, 2015, now U.S. Pat. No. 9,713,469, issued Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
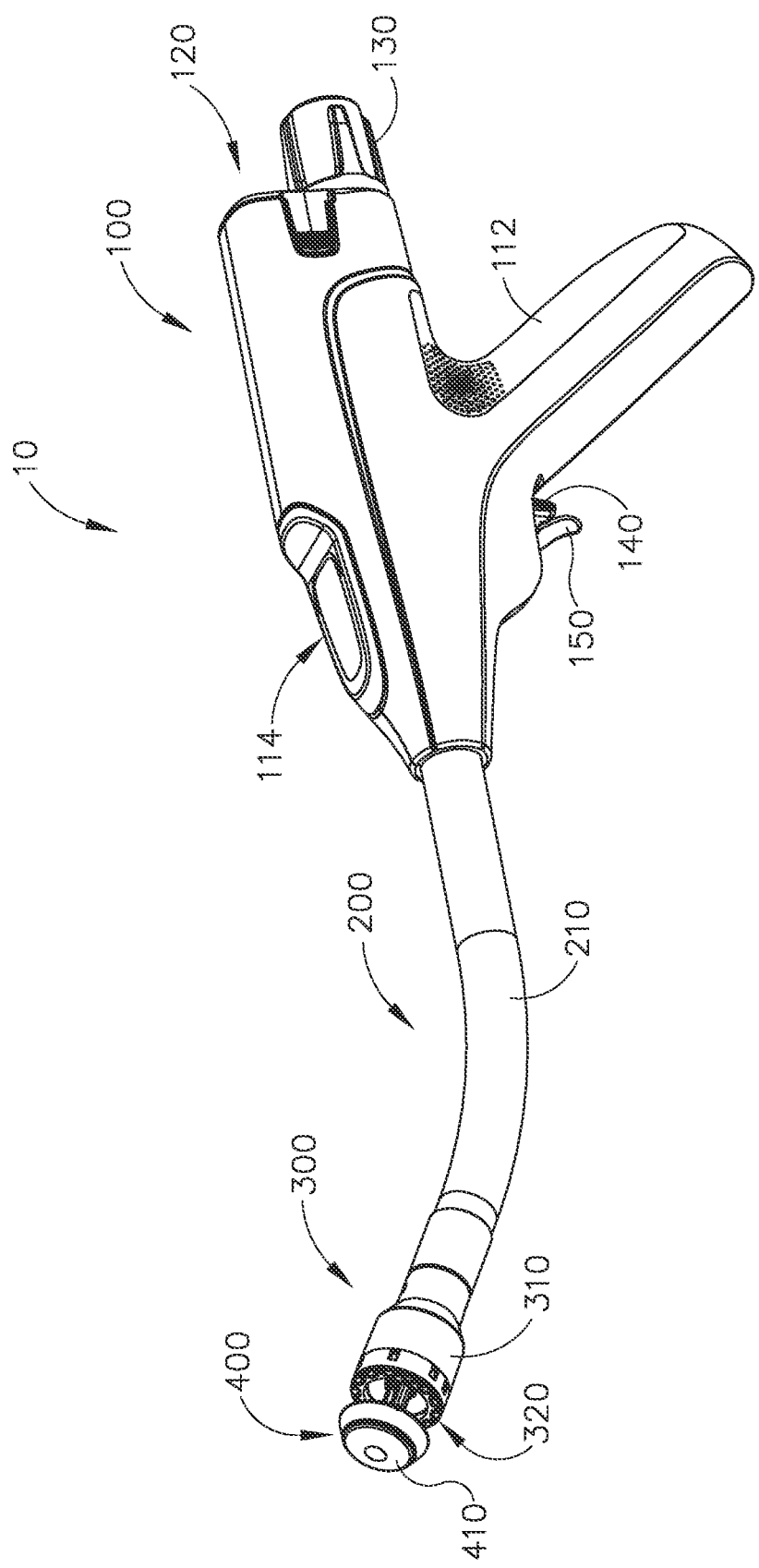
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. Overview of Exemplary Circular Stapling Surgical Instrument

A. Exemplary Circular Stapling Surgical Instrument

Figure 2:
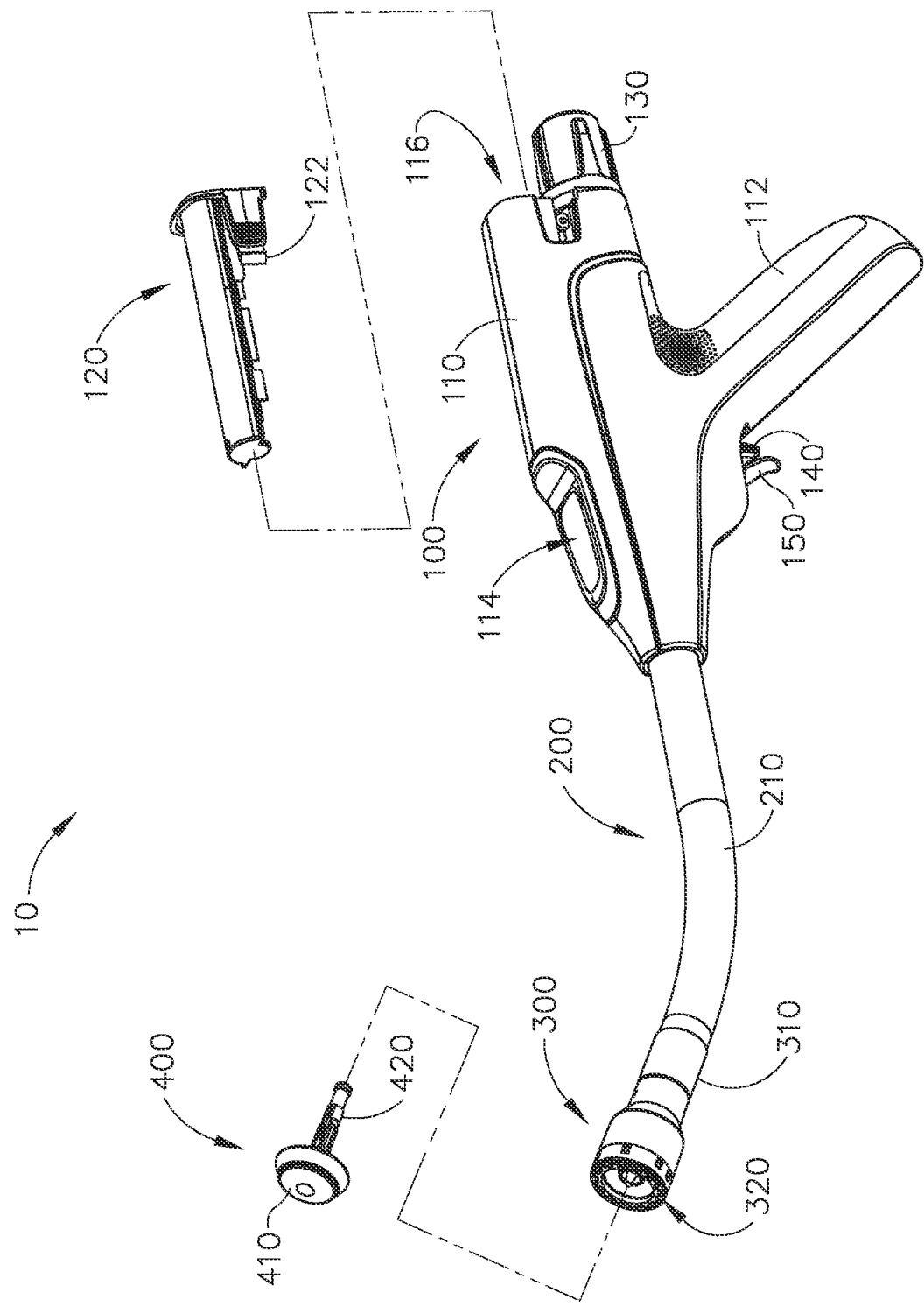
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114) that permits viewing of a movable indicator needle (not shown) as will be described in greater detail below. In some versions, a series of hash marks, colored regions, and/or other fixed indicators are positioned adjacent to user feedback feature (114) in order to provide a visual context for indicator needle.

Instrument (10) includes a battery pack (120). Battery pack (120) is operable to provide electrical power to a motor (160) in pistol grip (112). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein.

Stapling head assembly (300) is located at the distal end of shaft assembly (200). As shown in FIGS. 1-2, anvil (400) is configured to removably couple with shaft assembly (200), adjacent to stapling head assembly (300). Anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
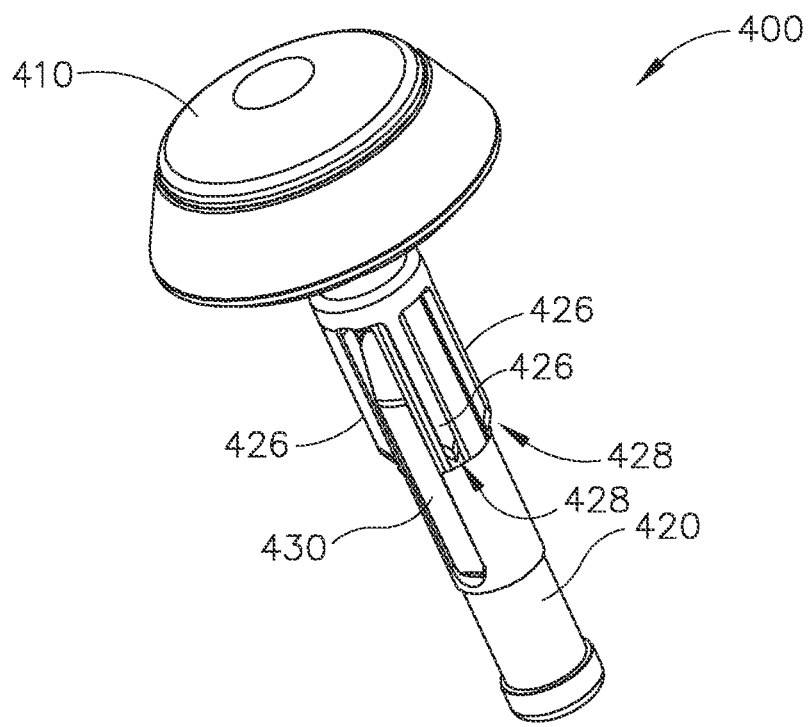
FIG. 3 depicts a perspective view of the anvil of the circular stapler of FIG. 1.
Figure 4:
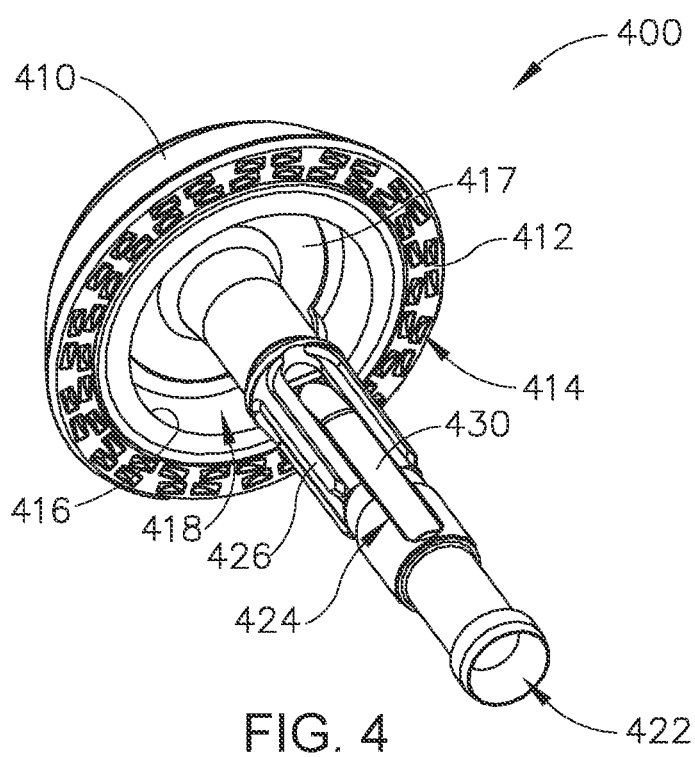
FIG. 4 depicts another perspective view of the anvil of FIG. 3.
Figure 5:
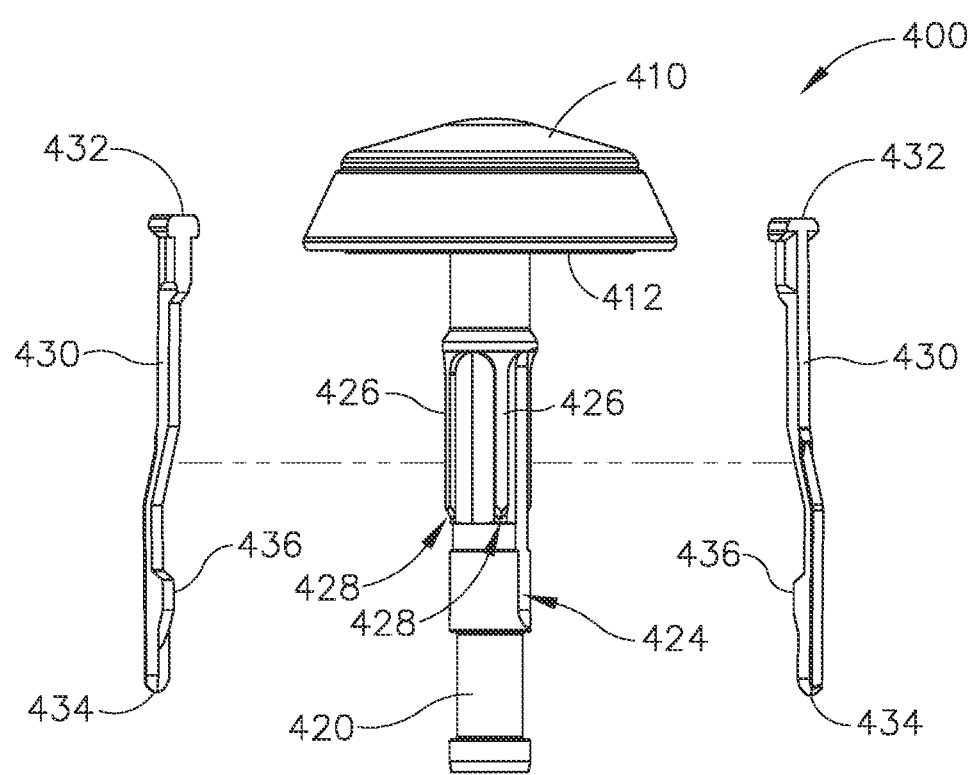
FIG. 5 depicts an exploded side elevational view of the anvil of FIG. 3.
Figure 6:
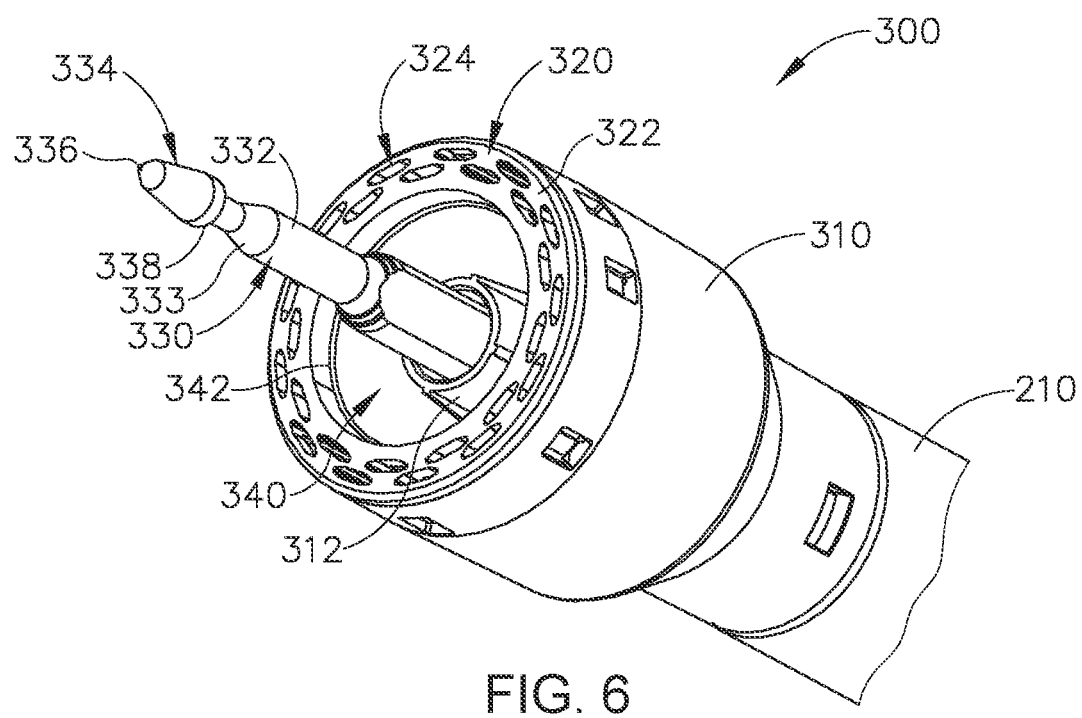
FIG. 6 depicts a perspective view of the stapling head assembly of the circular stapler of FIG. 1.

As shown in FIGS. 3-5, anvil (400) includes a head (410) and a shank (420). Head (410) includes a proximal surface (412) that defines an annular array of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to pivot radially inwardly toward the longitudinal axis defined by shank (420). Latch members (430) thus act as retaining clips. This allows anvil (400) to be removably secured to an anvil coupling projection in the form of a trocar (330) of stapling head assembly (300) as will be described in greater detail below. When shank (420) is secured to trocar (330) and trocar (330) is retracted proximally, the inner diameter of bore (314) in inner core member (312) of body member (310) laterally constrains latch members (430) to maintain engagement between latch shelves (436) and proximal surface (338) of head (334) of trocar (330). This engagement prevents anvil (400) from being released from trocar (330) during firing of stapling head assembly (300). It should be understood, however, that latch members (436) are merely optional. Anvil (400) may be removably secured to a trocar (330) using any other suitable components, features, or techniques. As shown in FIG. 4, anvil (400) of the present example includes a breakable washer (417) within annular recess (418). This washer (417) is broken by knife member (340) when the knife member (340) completes a full distal range of motion.

As shown in FIGS. 3-4, shank (420) of the present example includes a set of longitudinally extending splines (426) that are spaced about shank (420) in an angular array. The proximal end of each spline (426) includes a respective lead-in edge (428). As described in greater detail below, splines (426) are configured to engage corresponding splines (316) of an inner body member (310) of stapling head assembly (300) in order to consistently provide a predetermined angular alignment between anvil (400) and stapling head assembly (300). As also described below, this angular alignment may ensure that staple forming pockets (414) of anvil (400) are consistently angularly aligned appropriately with staple openings (324) of stapling head assembly (300). Thus, in the present example, splines (426) are precisely and consistently positioned in relation to staple forming pockets (414). In versions where head (410) and shank (420) are initially formed as separate pieces and then later joined together, the machine or other device that is used to join head (410) and shank (420) together may have appropriate indexing capabilities in order to reliably and consistently achieve the proper angular positioning of head (410) and shank (420) to thereby provide precise and consistent positioning of splines (426) in relation to staple forming pockets (414). Various suitable ways in which such results may be achieved will be apparent to those of ordinary skill in the art in view of the teachings herein. In some other versions, head (410) and shank (420) are formed together simultaneously, as a single unitary construction.

C. Exemplary Stapling Head Assembly

Figure 7:
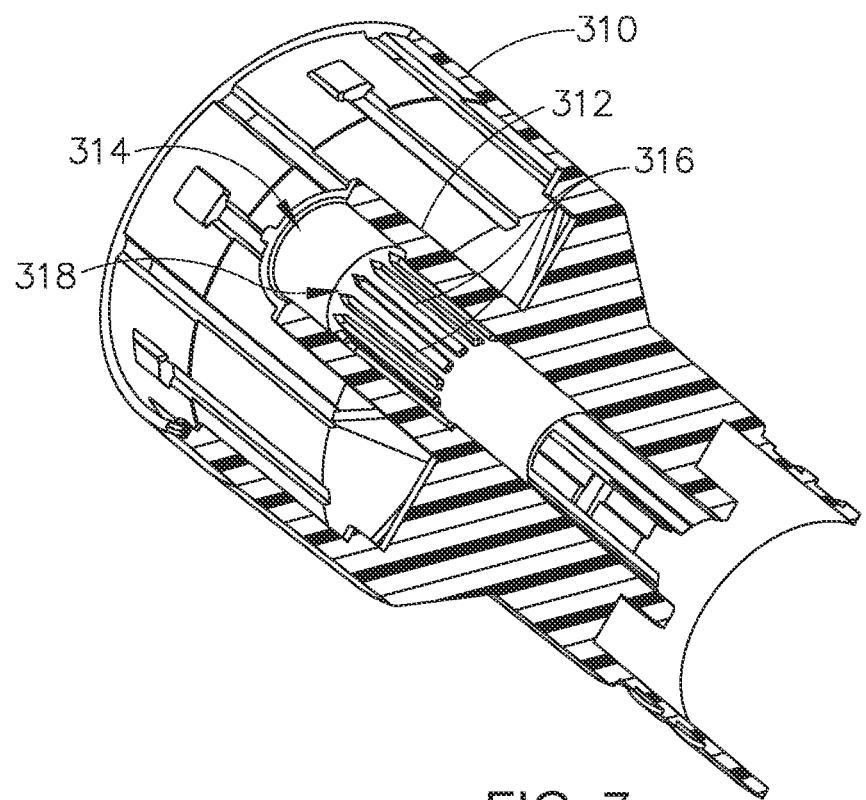
FIG. 7 depicts a perspective sectional view of an inner body member of the stapling head assembly of FIG. 6.
Figure 8:
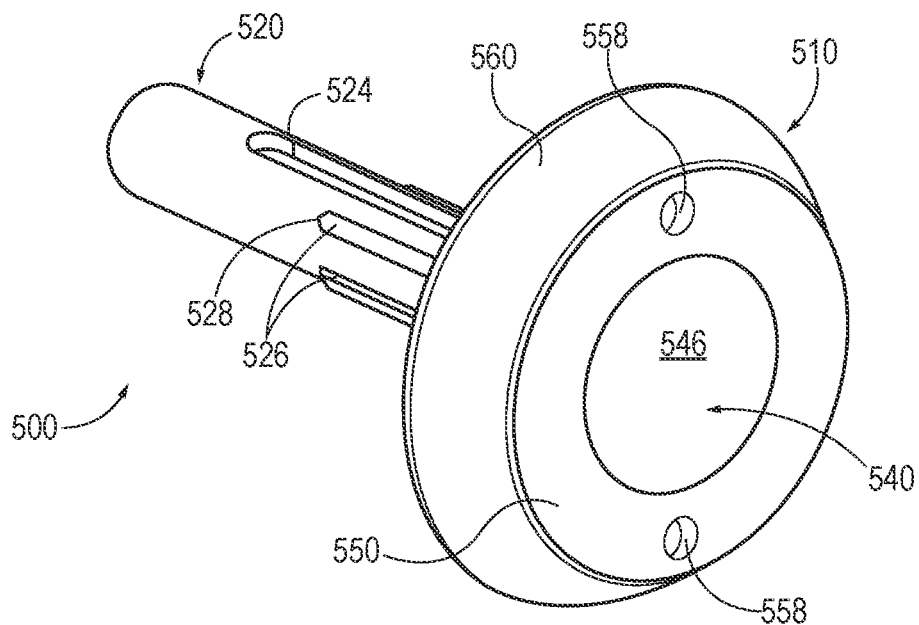
FIG. 8 depicts a perspective view of a first exemplary alternative anvil that may be incorporated into the circular stapler of FIG. 1.

As best seen in FIGS. 7-8, stapling head assembly (300) of the present example is coupled to a distal end of shaft assembly (200) and comprises a body member (310) and a slidable staple driver member (not shown). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

As shown in FIG. 7, inner core member (312) of body member (310) defines a bore (314). A plurality of longitudinally extending splines (316) are equidistantly spaced in an angular array within bore (314). The distal ends of splines (316) include lead-in edges (318) that are configured to complement lead-in edges (428) of splines (426) on shank (420) of anvil (400). In particular, after shank (420) is secured to trocar (330) as described in greater detail below, and as anvil (420) is thereafter retracted proximally relative to stapling head assembly (300) as also described in greater detail below, lead-in edges (318, 428) may cooperatively engage each other to drive anvil (400) to rotate relative to trocar (330) to angularly align splines (426) of anvil (400) with the gaps between splines (316) of body member (310). The gaps between splines (316) may be configured to have a width that is substantially equal to the width of splines (426). In this manner, when splines (426) of anvil (400) are positioned within the gaps between splines (316) of body member (310), anvil (400) may achieve a predetermined angular alignment relative to stapling head assembly (300). This predetermined angular alignment may ensure that staple openings (324) of deck member (320) are precisely aligned with corresponding staple forming pockets (414) of anvil (400). Thus, splines (316, 426) are configured to cooperate with each other to ensure that staples ejected through staple openings (324) are accurately driven into corresponding staple forming pockets (414, 510, 530) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). Trocar (330) includes a colored region (333). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430). Knife member (340) includes a distally presented, sharp circular cutting edge (342). Knife member (340) also defines an opening that is configured to coaxially receive core member (312) of body member (310).

A deck member (320) is fixedly secured to body member (310). Deck member (320) includes a distally presented deck surface (322) defining two concentric annular arrays of staple openings (324). Staple openings (324) are arranged to correspond with the arrangement of staple drivers and staple forming pockets (414) described above. Thus, each staple opening (324) is configured to provide a path for a corresponding staple driver to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein. As best seen in FIG. 7, deck member (320) defines an inner diameter that is just slightly larger than the outer diameter defined by knife member (340). Deck member (320) is thus configured to allow knife member (340) to translate distally to a point where cutting edge (342) is distal to deck surface (322).

II. Exemplary Anvils and Methods of Manufacture

As described above, anvil (400) of instrument (10) may be machined as a single unitary component or anvil (400) may be manufactured by initially forming head (410) and shank (420) as separate pieces and then later joining head (410) and shank (420) together. Because head (410) and shank (420) may be initially formed as separate pieces, it may be desirable to strengthen the coupling between head (410) and shank (420). Additionally, it may be desirable to make head (410) and shank (420) using different manufacturing processes and in a low-cost manner. Moreover, it may be desirable to refine certain portions and surfaces of head (410) and/or shank (420) to improve the operability anvil (400) with instrument (10). Therefore, it may therefore be desirable to manufacture exemplary anvils (500, 600, 700) that address these and other shortcomings, while also enabling anvils (500, 600, 700) to function interchangeably with anvil (400) described above with reference to FIGS. 1-5.

As will be described with reference to FIGS. 9-20, surgical instrument (10) includes anvil (500, 600, 700), that is intended to be used in place of anvil (400) described above with reference to FIGS. 1-5. As previously described, surgical instrument (10) includes a body (shown as handle assembly (100)), shaft assembly (200) extending distally from handle assembly (100), stapling head assembly (300), and anvil (400). Stapling head assembly (300) is positioned at a distal end of shaft assembly (200). Stapling head assembly (300) includes an anvil coupling feature (shown as trocar (330)), at least one annular array of staples, and the staple driver. As will be described in greater detail below and similar to the functionality of anvil (400), anvils (500, 600, 700) are each configured to couple with trocar (330) and each are configured to deform staples driven by the staple driver.

A. First Exemplary Alternative Anvil

FIGS. 9-12 show various perspective views of a first exemplary anvil (500) that may be incorporated into instrument (10) of FIG. 1. Anvil (500) includes a head (510) and a shank (520). Shank (520) extends proximally from head (510) and is configured to be coupled with head (510) once formed. Head (510) includes a proximal surface (512) that defines an annular array of staple forming pockets (514) shown in FIG. 10. As shown, staple forming pockets (514) are arranged in two concentric annular arrays, similar to those shown in FIG. 16. Alternatively, staple forming pockets (514b) may be arranged in three or more concentric annular arrays, similar to those shown in FIG. 17.

Figure 10:
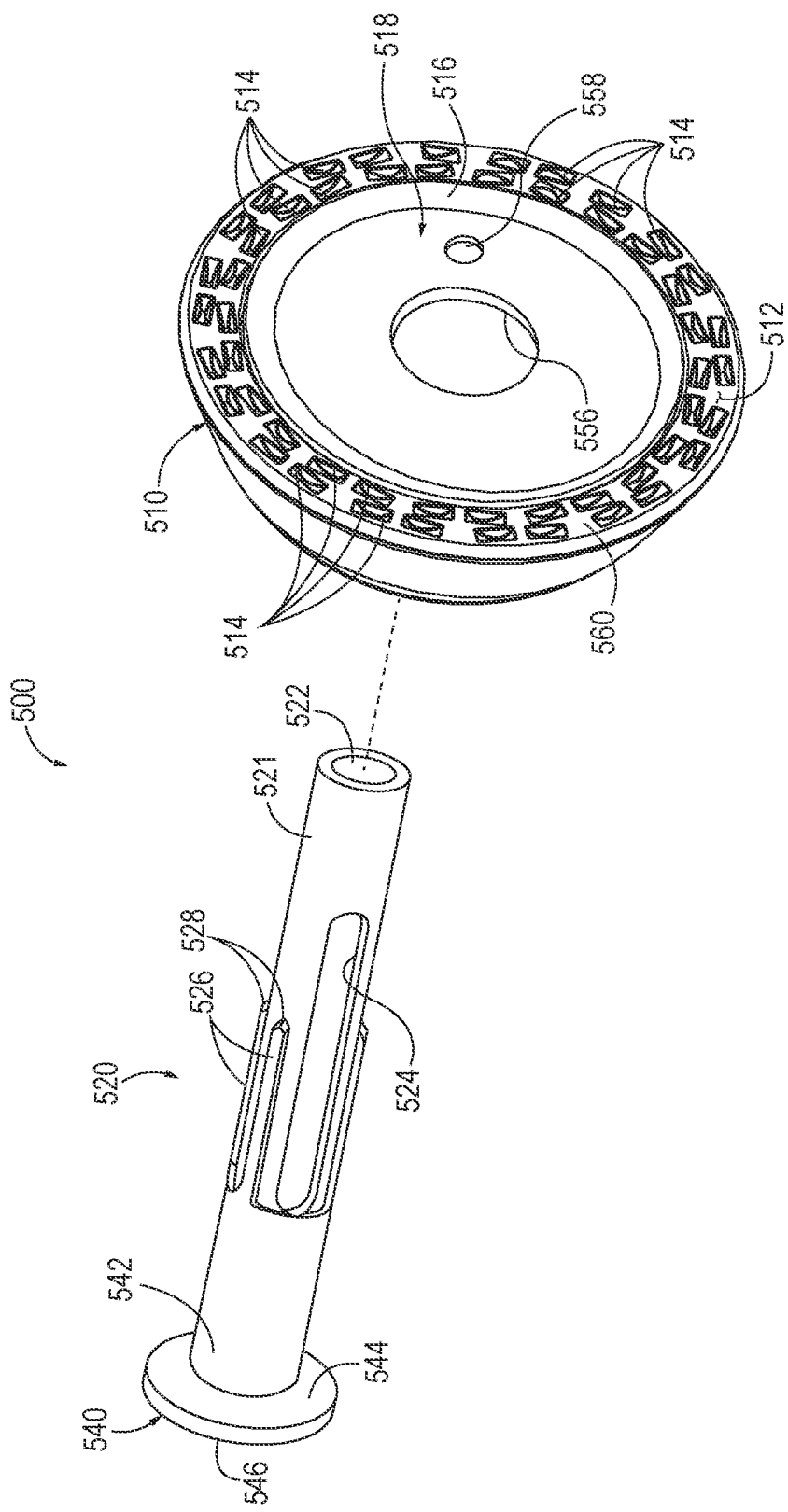
FIG. 10 depicts an exploded perspective view of the shank and the head of the anvil of FIG. 8, where the head includes an annular array of staple forming pockets.
Figure 11:
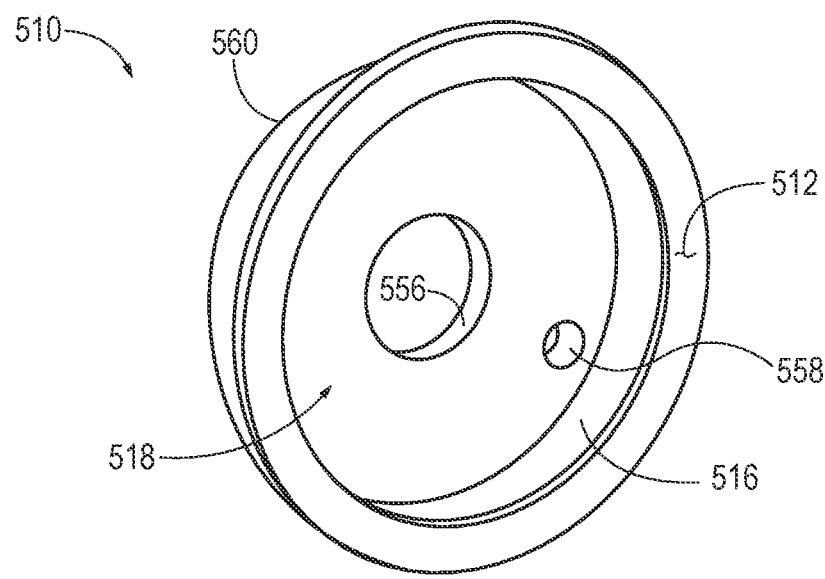
FIG. 11 depicts a perspective view of the head of FIG. 10, but where the annular array of staple forming pockets are not yet formed.

Staple forming pockets (514) are configured to deform the staples as the staples are driven into staple forming pockets (514). For instance, each staple forming pocket (514) may deform a generally "U" shaped staple into a "B" shape as is known in the art. As shown in FIGS. 10 and 11, proximal surface (512) of head (510) terminates at an inner edge (516), which defines an outer boundary of an annular recess (518) surrounding shank (520). As will be described in greater detail with reference to FIG. 10, head (510), including staple forming pockets (514), may be formed using an injection molding process, such as a metal injection molding process. Metal injection molding (MIM) refers to any metalworking process where finely-powdered metal is mixed with a binder material to create a feedstock that is subsequently shaped and solidified using molding process (such as injection molding). Metal injection molding allows for high volume, complex parts to be shaped. Alternatively, head (510) may be formed from a polymeric material using an injection molding process. As will be described in greater detail with reference to FIGS. 13A-16, at least a portion of at least one staple forming pocket (514) may be coined or electrochemically machined to improve one or more properties of staple forming pockets (514).

Shank (520) includes a longitudinally extending body (521) that defines a bore (522) and may include a pair of pivoting latch members (not shown) positioned in bore (522), that may be similar in structure and function to latch members (430) described above with reference to shank (420) of anvil (400). The latch members are positioned within bore (522) such that the distal ends are positioned at the proximal ends of lateral openings (524), which are formed through the sidewall of shank (520). Lateral openings (524) provide clearance for the latch member to deflect radially outwardly from the longitudinal axis defined by shank (520). The latch members allow anvil (500) to be removably secured to a trocar (330) of stapling head assembly (300). When shank (520) is secured to trocar (330) and trocar (330) is retracted proximally, the inner diameter of bore (314) in inner core member (312) of body member (310) laterally constrains the latch members to maintain engagement with proximal surface (338) of head (334) of trocar (330). This engagement prevents anvil (500) from being released from trocar (330) during firing of stapling head assembly (300). The latch members may be omitted, such that anvil (500) may be removably secured to a trocar (330) using any other suitable components, features, or techniques.

Figure 9:
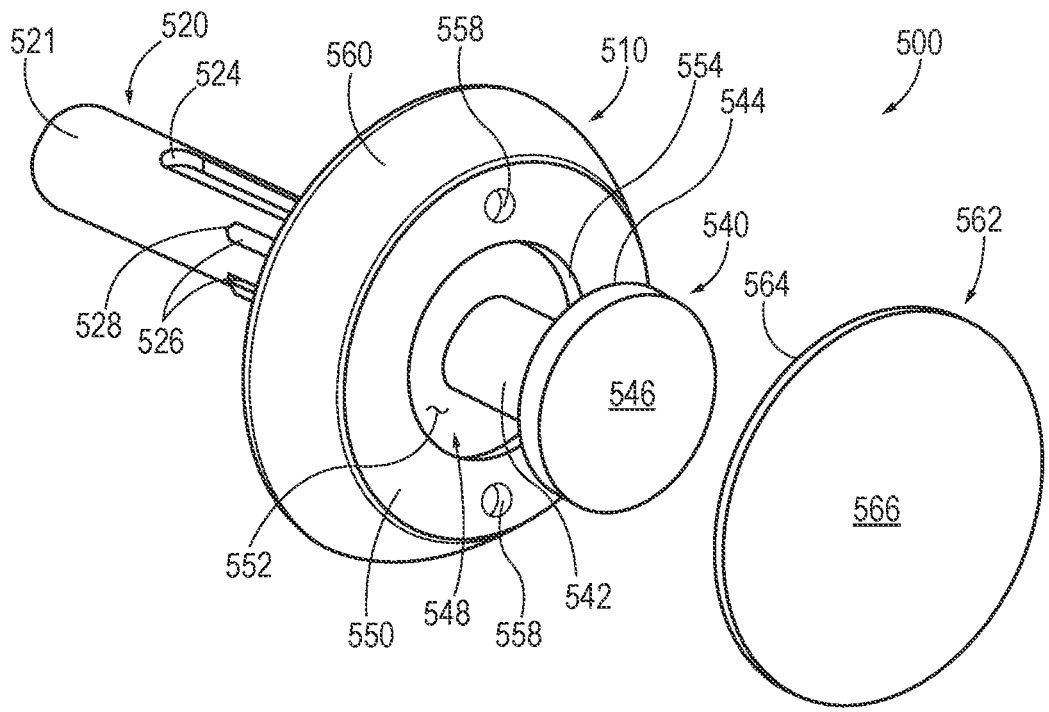
FIG. 9 depicts an exploded perspective view of the anvil of FIG. 8, where the anvil includes a shank, a head, and a cap.

As shown in FIGS. 8-10, shank (520) includes a set of longitudinally extending splines (526) that are spaced about shank (520) in an angular array. The proximal end of each spline (526) includes a respective lead-in edge (528). Splines (526) are configured to engage corresponding splines (316) of an inner body member (310) of stapling head assembly (300) to consistently provide a predetermined angular alignment between anvil (500) and stapling head assembly (300). This angular alignment may ensure that staple forming pockets (514) of anvil (500) are consistently angularly aligned appropriately with staple openings (324) of stapling head assembly (300). Thus, splines (526) are precisely and consistently positioned in relation to staple forming pockets (514). As shown in FIG. 9, shank (520) further includes a flange (540) extending radially outward from a distal end (542) of shank (520). As a result, flange (540) has a larger area than longitudinally extending body (521) of shank (520). Flange (540) includes opposing proximal and distal surfaces (544, 546). As described in greater detail with reference to FIG. 20, shank (520) may be machined using one or more machining processes.

Figure 12:
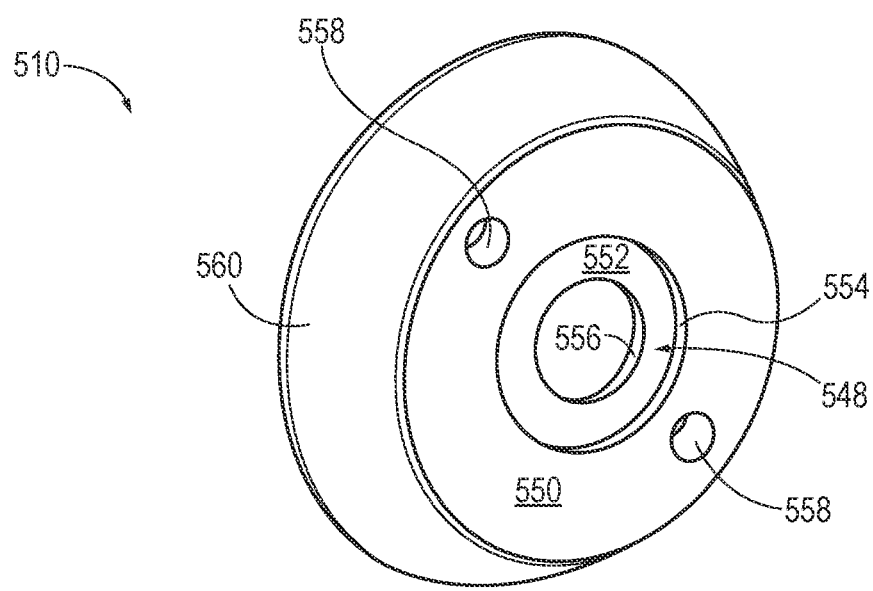
FIG. 12 depicts another perspective view of the head of FIG. 11.

As shown in FIGS. 9 and 12, head (510) includes a recessed portion (548) that extends proximally from a distal outer surface (550). Recessed portion (548) includes a recessed surface (552) surrounded by an annular wall (554), with an aperture (556) extending through recessed surface (552) that is configured to receive longitudinally extending body (521) of shank (520). As shown, aperture (556) is concentric to both distal outer surface (550) and recessed surface (552); however, other positionings of aperture (556) relative to distal outer surface (550) and recessed surface (552) are also envisioned. As shown in FIGS. 8-10, recessed portion (548) is sized and configured to receive flange (540) of shank (520). While recessed portion (548) and flange (540) are shown as circular, it is also envisioned that recessed portion (548) and flange (540) may have a variety of other shapes (e.g. rectangular) that may prevent relative rotation of head (510) and shank (520), if desired.

Distal outer surface (555) also includes one or more recesses (558), with two being shown, which may be used to secure a distal feature (such as a cap). Head (510) may also include a tapered portion (560) extending proximally from distal outer surface (550). Tapered portion (560) is shown as a chamfer. Recessed surface (552) of recessed portion (548) may be in direct contact with proximal surface (544) of flange (520) once head (510) is coupled with shank (520). As shown in FIG. 8, distal outer surface (550) of head (510) is generally flush with distal surface of flange (540) after head (510) is coupled with shank (520). In other words, the depth of recessed portion (548) is about the same as the thickness of flange (540). However, the depth of recessed portion (548) and/or the thickness of flange (540) may vary. Additionally, distal outer surface (550) may be arcuate, if desired.

As shown in FIG. 9, head (510) may be coupled to shank (520) using a cap (562), shown as a thin anvil plate. Cap (562) is configured to sandwich flange (540) of shank (520) between cap (562) and head (510). Cap (562) includes proximal and distal surfaces (564, 566). According to an embodiment, cap (562) may be a material (e.g. polymeric material) overmolded onto head (510) using one or more overmolding processes. More specifically, cap (562) may be overmolded onto distal surface (546) of flange (540) and/or distal outer surface (550) of head (510). As a result, cap (562) may not be a separate component. Alternatively, cap (562) may be selectively coupleable to head (510) using one or more securement features that are configured to couple with recess (558). As shown, cap (562) is formed from a polymeric material; however, cap (562) may be formed from any suitable material.

Staple forming pockets (514) may be formed simultaneously with or after head (510) is formed. For example, FIGS. 11 and 12 show perspective views of head (510), but with staple forming pockets (514) not yet formed. As described in greater detail with reference to FIG. 20, at least a portion of head (510) may be machined after forming head (510) if desired.

Figure 13A:
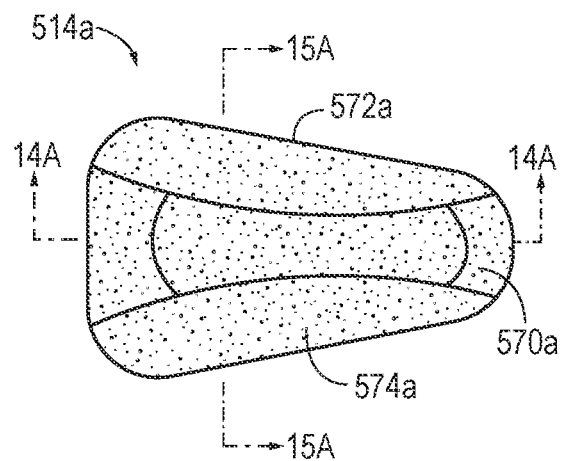
FIG. 13A depicts a staple forming pocket prior to being coined or electrochemically machined.

As shown in FIGS. 13A-16, at least a portion of staple forming pocket (514) may be coined or electrochemical machined after forming staple forming pocket (514) using an injection molding process (e.g. a metal injection molding process). More specifically, FIG. 13A shows a staple forming pocket (514a) prior to being coined or electrochemically machined, while FIG. 13B shows the staple forming pocket (514) of FIG. 13A, after being coined or electrochemically machined. As shown in FIG. 13A, staple forming pocket (514a) includes a central portion (570a) disposed between outer portions (572a, 574a). As shown in FIGS. 13B, 14B, and 15B, central portion (570) of staple forming pocket (514) is subsequently coined or electrochemically machined, which results in a smoother surface and a denser surface than another portion (e.g. outer portions (572, 574)) that was not coined or electrochemical machined. As a result, outer portions (572, 574) have surface that is rougher and less dense than central portion (570) of staple forming pocket (514). Alternatively, the entire staple forming pocket (514), including outer portions (572, 574), may be coined or electrochemically machined, if desired.

Coining is a form of precision stamping where a workpiece is subjected to a sufficiently high stress to induce plastic flow on the surface of the material. The plastic flow reduces surface grain size and work hardens the surface of the workpiece, while the material deeper within the workpiece retains its toughness and ductility. Coining also improves the dimensional tolerances of staple forming pocket (514). Electrochemical machining (ECM) is a method of removing metal using one or more electrochemical processes. Electrochemical machining may be used for mass production due to cost effectiveness and is utilized for working extremely hard materials or materials that are difficult to machine using conventional methods. Electrochemical machining may cut small or uniquely-shaped angles, intricate contours, or cavities in hard metals workpieces.

Figure 13B:
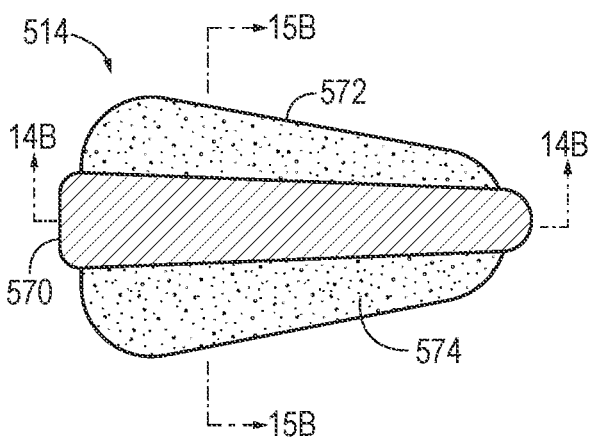
FIG. 13B depicts the staple forming pocket of FIG. 13A, but after being coined or electrochemically machined.
Figure 14A:
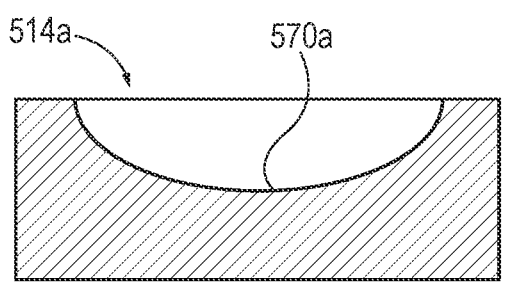
FIG. 14A depicts a central portion of the staple forming pocket of FIG. 13A, taken along line 14A-14A of FIG. 13A.
Figure 14B:
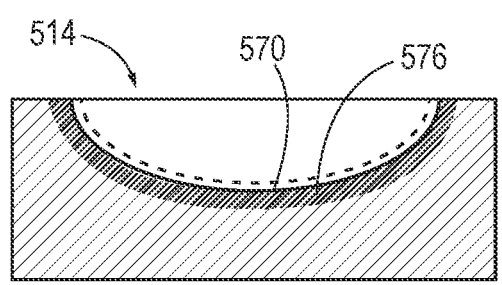
FIG. 14B depicts a central portion of the staple forming pocket of FIG. 13B, taken along line 14B-14B of FIG. 13B.

FIG. 14A shows central portion (570a) of staple forming pocket (514a) taken along line 14A-14A of FIG. 13A, while FIG. 14B shows central portion (570) of staple forming pocket (514), taken along line 14B-14B of FIG. 13B. As shown when comparing FIG. 14A with FIG. 14B, central portion (570a) having been coined or electrochemically machined is both smoother and denser than another portion (e.g. outer portions (572, 574)) of the same staple forming pocket (514) that was not coined or electrochemically machined.

Figure 15A:
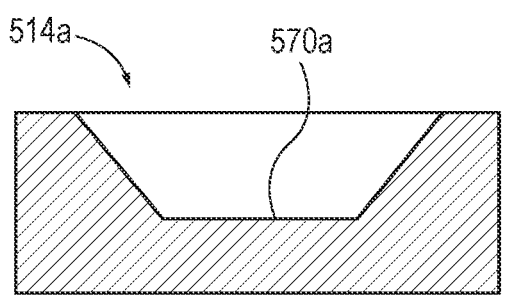
FIG. 15A depicts a portion of the staple forming pocket of FIG. 13A, taken along line 15A-15A of FIG. 13A.
Figure 15B:
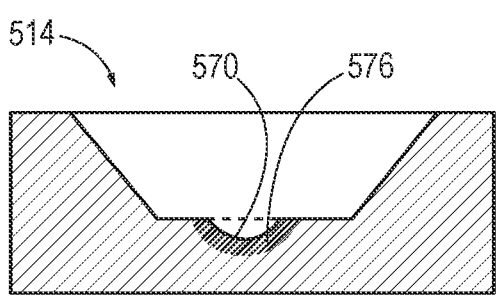
FIG. 15B depicts a portion of the staple forming pocket of FIG. 13B, taken along line 15B-15B of FIG. 13B.
Figure 16:
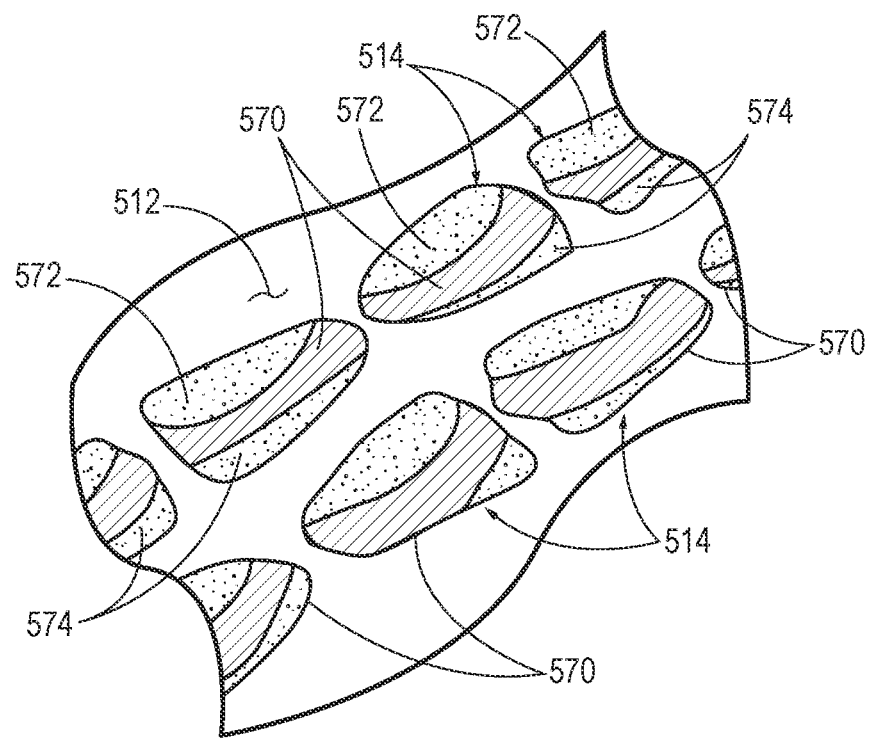
FIG. 16 depicts an annular array of individual staple forming pockets of FIG. 13B after being coined or electrochemically machined.

FIG. 15A shows a portion of staple forming pocket (514a) of FIG. 13A, taken along line 15A-15A, while FIG. 15B shows a portion of staple forming pocket (514) of FIG. 13B, taken along line 15B-15B. As shown when comparing FIG. 15A with FIG. 15B, a channel (576) results after the coining or electrochemical machining process. FIG. 16 shows an annular array of staple forming pockets (514) of FIG. 13B, after being coined or electrochemically machined. More specifically, central portions (570) are coined or electrochemically machined.

Figure 17:
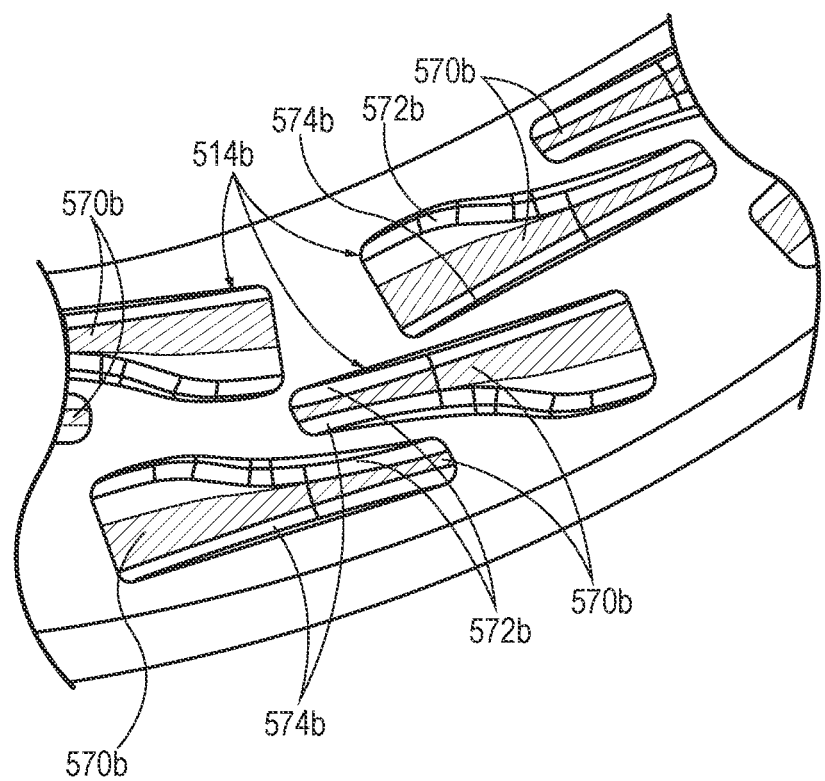
FIG. 17 depicts another annular array of individual staple forming pockets after being coined or electrochemically machined.

FIG. 17 shows another an annular array of staple forming pockets (514b) after being coined or electrochemically machined. Similar to staple forming pockets (514), staple forming pockets (514b) also include a central portion (570b) and outer portions (572b, 574b). As shown, a central portion (570b) is coined or electrochemically machined, and as a result, is both smoother and denser than another portion (e.g. outer portions (572b, 574b)) of same staple forming pocket (514b) that is not coined or electrochemically machined.

B. Second Exemplary Alternative Anvil

Figure 18:
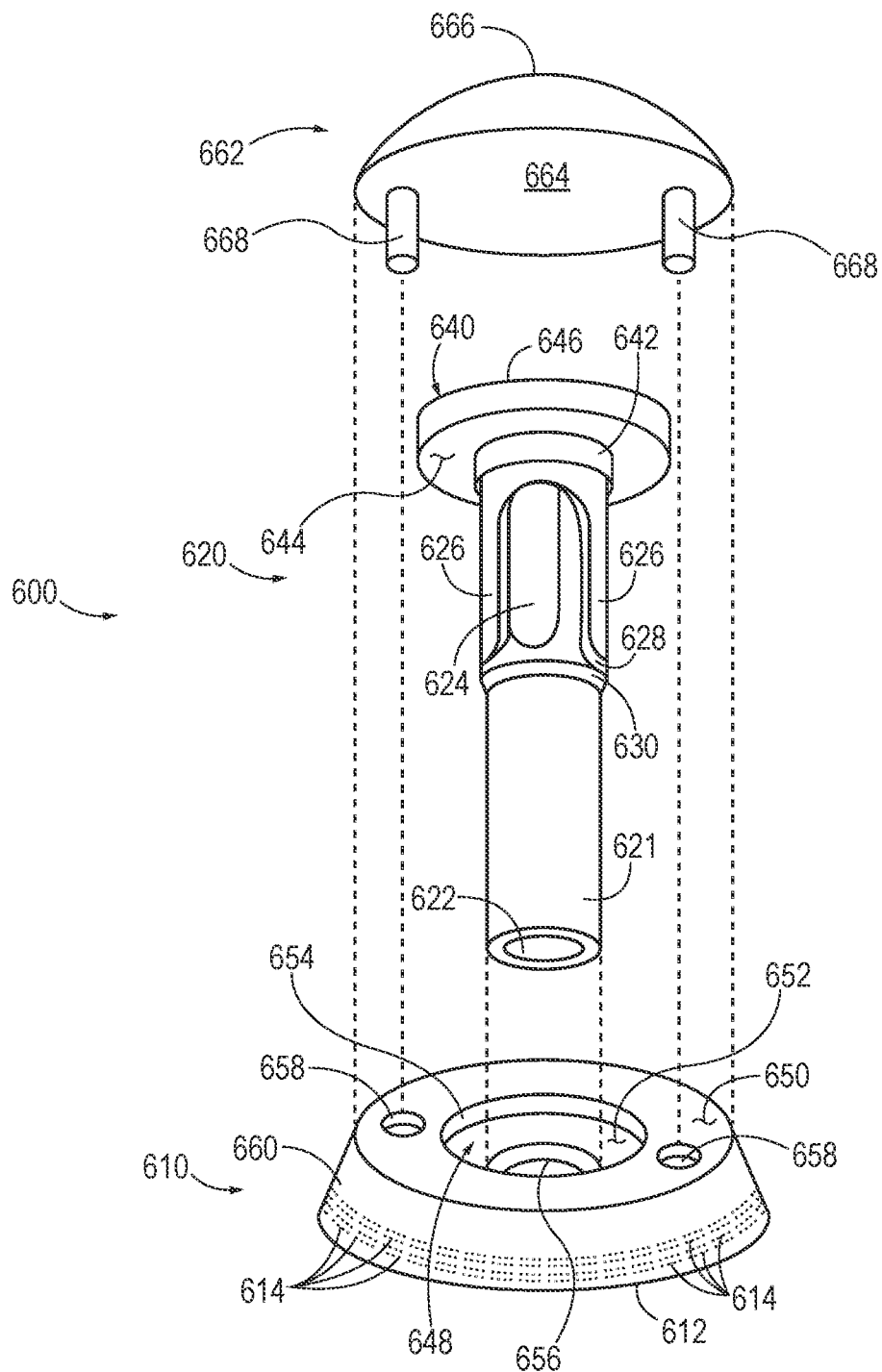
FIG. 18 depicts a perspective exploded view of a second exemplary alternative anvil that may be incorporated into the circular stapler of FIG. 1.

FIG. 18 shows a perspective view of a second exemplary anvil (600) that may be incorporated into instrument (10) of FIG. 1 in place of anvil (400, 500) described above. Similar to anvil (500), anvil (600) includes a head (610), a shank (620), and a cap (662). As discussed in greater detail below, unlike cap (562), cap (662) includes one or more engagement features. Similar to head (510), head (610) includes a proximal surface (612), staple forming pockets (614), a recessed portion (648), a distal outer surface (650), a recessed surface (652), an annular wall (654), an aperture (656), recesses (658), and a tapered portion (660). Similar to shank (520), shank (620) includes a bore (622), lateral openings (624), a set of longitudinally extending splines (626), lead-in edges (628), a flange (640), and a distal end (642). Similar to flange (540), flange (640) includes opposing proximal and distal surfaces (644, 646). Similar to cap (562), cap (662) includes opposing proximal and distal surfaces (664, 666).

Proximal surface (612) of head (610) defines an annular array of staple forming pockets (614), which are similar to those shown in FIG. 10. As described in greater detail with reference to FIG. 20, head (610), including staple forming pockets (614), may be formed using a metal injection molding process and subsequently machined using one or more machining processes. As previously described with reference to staple forming pocket (514) in FIGS. 13A-16, at least a portion of at least one staple forming pocket (614) may be coined or electrochemically machined to improve one or more properties of staple forming pockets (614). Recessed portion (648) of head (610) extends proximally from distal outer surface (650). Recessed surface (652) is surrounded by annular wall (654), with aperture (656) extending through recessed surface (652). Aperture (656) is configured to receive longitudinally extending body (621) of shank (620) therethrough. Recessed portion (648) is sized and configured to receive flange (640) of shank (620). Recessed portion (648) of head (610) may be in direct contact with proximal surface (644) of flange (620), once head (610) is coupled with shank (620). Distal outer surface (655) of head (610) also includes one or more recesses (658), with two being shown, which may be used to secure a distal feature, such as cap (662). Tapered portion (660) extends proximally from distal outer surface (650).

As shown in FIG. 18, shank (620) extends proximally from head (610) and is configured to be coupled with head (610) once formed. While not shown in FIGS. 8-12, shank (620) includes an outwardly extending portion (630). As shown in FIG. 18, flange (640) extending radially outward from distal end (642) of shank (620). Flange (640) includes opposing proximal and distal surfaces (644, 646). As described in greater detail with reference to FIG. 20, shank (620) may be formed using a metal injection molding process and subsequently machined using one or more machining processes. As a result, both head (610) and shank (620) may be separately formed using metal injection molding processes. Additionally, both head (610) and shank (620) may be separately machined after being formed from the respective metal injection molding processes.

Head (610) may be coupled to shank (620) using cap (662), shown in this exemplary embodiment as an arcuate cap. Cap (662) is configured to sandwich flange (640) of shank (620) between cap (662) and head (610). Unlike cap (562), cap (662) is selectively couplable to head (610) using one or more securement features. For example, cap (662) may include at least one proximally facing projection (668), that is configured to couple with at least one corresponding recess (658). As such, coupling cap (662) with head (610) includes inserting proximally facing projections (668) into recesses (658). While each recess (662) is shown as extending completely through distal outer surface (650), it is envisioned that recesses (658) may extend only partly through distal outer surface (650). While cap (662) is shown as being formed from a polymeric material; it is envisioned that cap (662) may be formed from any suitable material. As shown, distal surface (666) of cap (662) is rounded, forming a hemispherical shape.

C. Third Exemplary Alternative Anvil

Figure 19:
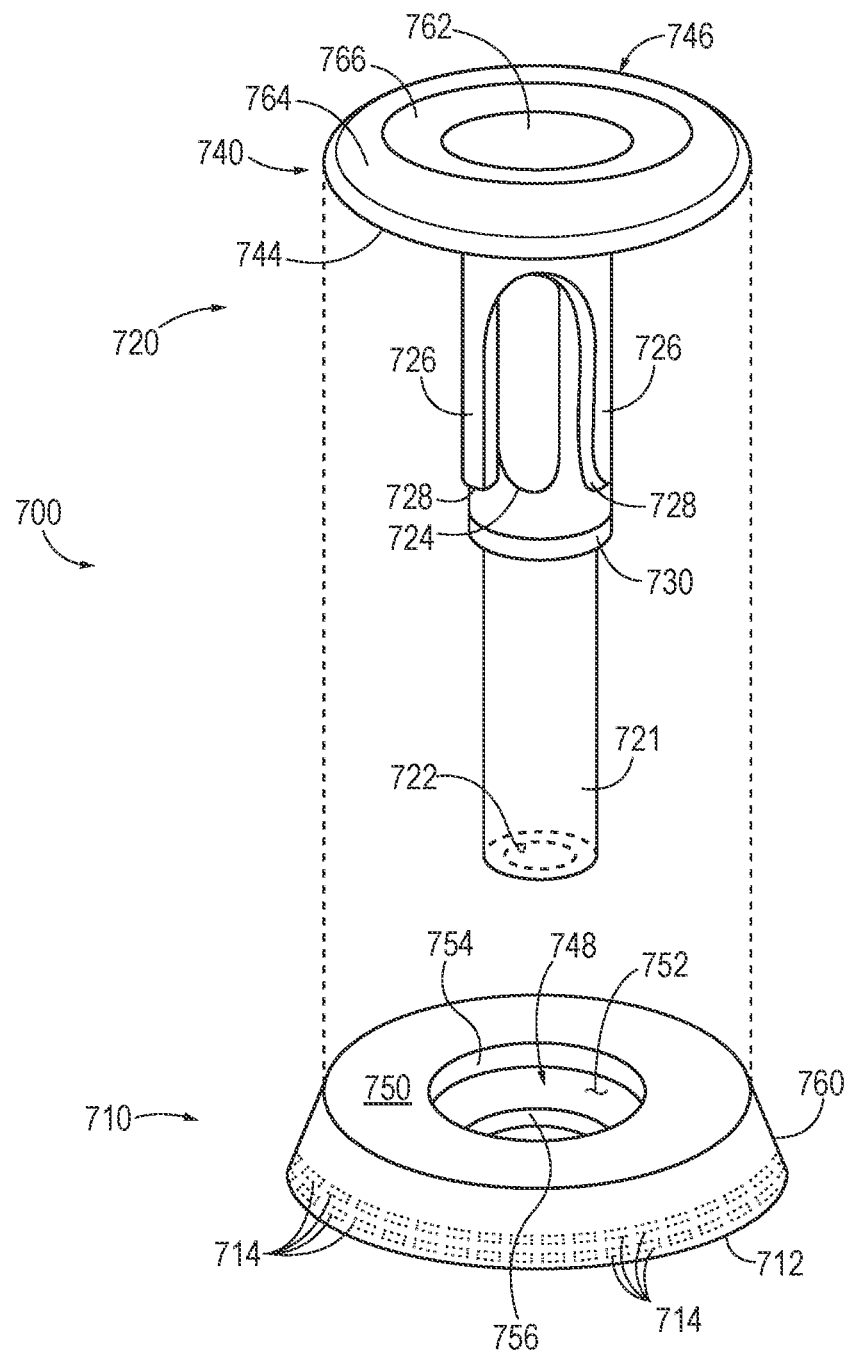
FIG. 19 depicts a perspective exploded view of a third exemplary alternative anvil that may be incorporated into the circular stapler of FIG. 1.

FIG. 19 shows a perspective view of a third exemplary anvil (700) that may be incorporated into instrument (10) of FIG. 1 in place of anvil (400, 500) described above. Similar to anvil (500), anvil (700) includes a head (710) and a shank (720). Similar to head (510), head (710) includes a proximal surface (712), staple forming pockets (714), a recessed portion (748), a distal outer surface (750), a recessed surface (752), an annular wall (754), an aperture (756), and a tapered portion (760). Similar to shank (520), shank (720) includes a bore (722), lateral openings (724), a set of longitudinally extending splines (726), lead-in edges (728), and a flange (740) and a distal end (742). Similar to flange (540), flange (740) includes opposing proximal and distal surfaces (744, 746).

Proximal surface (712) of head (710) defines an annular array of staple forming pockets (714), which are similar to those shown in FIG. 10. As described in greater detail with reference to FIG. 20, head (710), including staple forming pockets (714), may be formed using a metal injection molding process and subsequently machined using one or more machining processes. As previously described with reference to staple forming pocket (514) in FIGS. 13A-16, at least a portion of at least one staple forming pocket (714) may be coined or electrochemically machined to improve one or more properties of staple forming pockets (714). Recessed portion (748) of head (710) extends proximally from distal outer surface (750). Recessed surface (752) is surrounded by annular wall (754), with aperture (756) extending through recessed surface (752). Aperture (756) is configured to receive longitudinally extending body (721) of shank (720) therethrough. Recessed portion (748) is sized and configured to receive flange (740) of shank (720). Recessed surface (752) of recessed portion (748) may be in direct contact with proximal surface (744) of flange (720), once head (710) is coupled with shank (720). Tapered portion (760) extends proximally from distal outer surface (750).

As shown in FIG. 19, shank (720) extends proximally from head (710) and is configured to be coupled with head (710) once formed. While not shown in FIGS. 8-12, shank (720) includes an outwardly extending portion (730). As shown in FIG. 19, flange (740) extend radially outward from distal end (742) of shank (720). Flange (740) includes opposing proximal and distal surfaces (744, 746). Distal surface (746) of flange (740) includes an inner shallow portion (762) and a rounded outer edge portion (764). As shown, rounded outer edge portion (764) includes a distal most portion (766) that is the distal most point of shank (720). A proximal surface (744) of flange (740) is coupled with distal outer surface (750) of head (710). Shank (720) may be formed using a metal injection molding process and subsequently machined using one or more machining processes.

D. Exemplary Method of Manufacture

Figure 20:
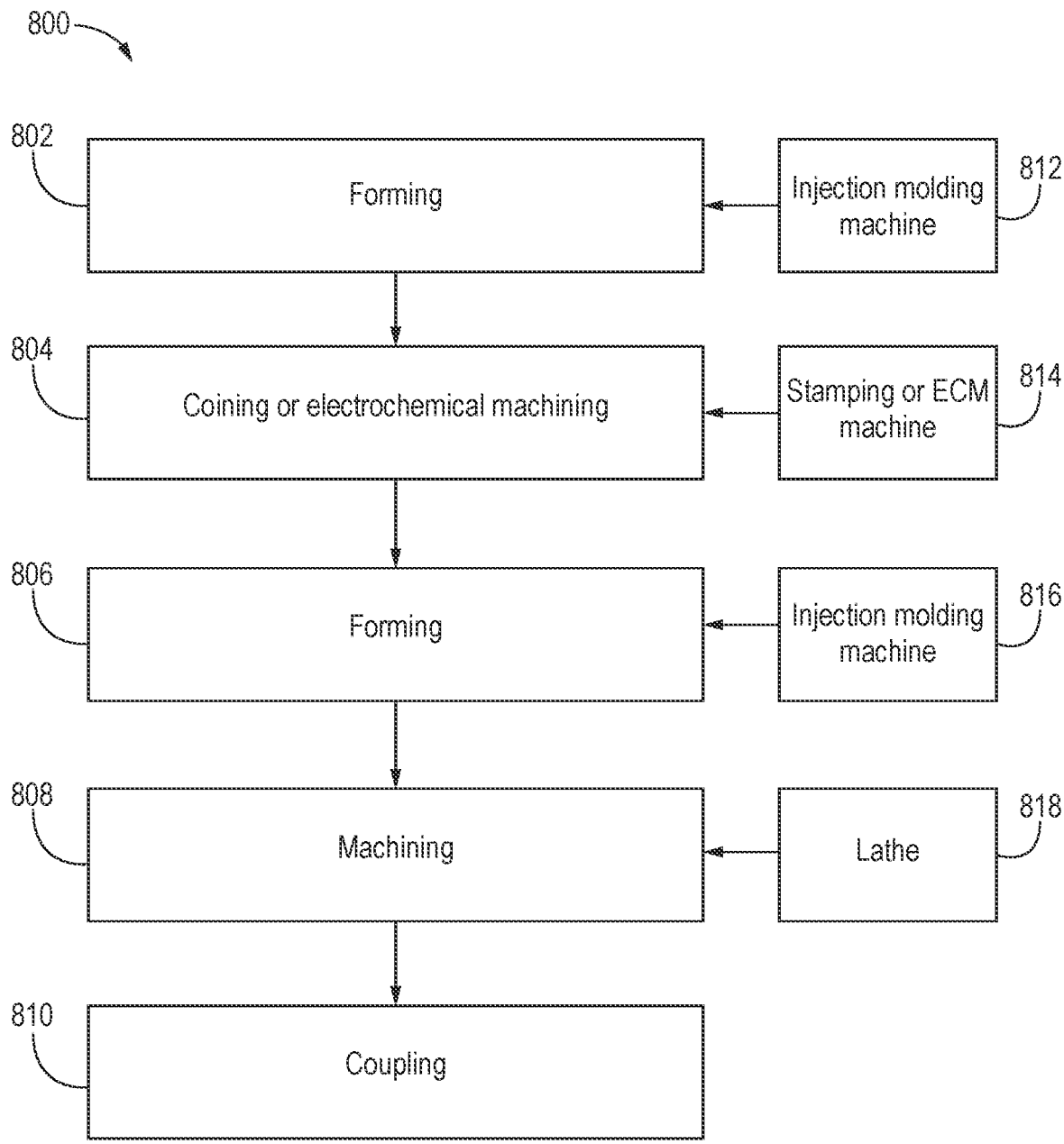
FIG. 20 depicts an exemplary method of manufacturing the anvil of FIG. 8 that may be incorporated into the circular stapler of FIG. 1.

FIG. 20 shows an exemplary method (800) of manufacturing anvils (500, 600, 700) that may be incorporated into instrument (10) of FIG. 1. As previously described, anvil (500, 600, 700) includes head (510, 610, 710) and shank (520, 620, 720) that extends proximally from head (510, 610, 710). At step (802), method (800) includes forming head (510, 610, 710), including staple forming pockets (514, 614, 714), using an injection molding machine (812). Staple forming pockets (514, 614, 714) may be formed simultaneously with or after head (510, 610, 710) is formed using a metal injection molding. For example, head (510, 610, 710) may be formed using a metal injection molding process using a metal injection molding machine. At step (804), method (800) includes machining at least a portion of head (510, 610, 710). Machining may include coining or electrochemical machining at least a portion of at least one staple forming pocket (514, 614, 714) using a stamping or ECM machine (814). As previously described, the portion of staple forming pocket (514, 614, 714) coined or electrochemically machined is both smoother and denser than another portion that was not coined or electrochemical machined. Other benefits may also be achieved.

At step (806), method (800) includes forming shank (520, 620, 720) using an injection molding machine (816). Injection molding machine (816) may be the same or different than injection molding machine (812). Shank (520, 620, 720) may be formed using a metal injection molding process using a metal injection molding machine. At step (808), method (800) includes machining shank (520, 620, 720) using a lathe (818). If desired, shank (520, 620, 720) may be machined from a single piece of material without being previously formed using an injection molding process.

At step (810), method (800) includes coupling head (510, 610, 710) with shank (520, 620, 720) that were separately manufactured. Coupling head (510, 610) with shank (520, 620) may include coupling cap (562, 662) with head (510, 610) to sandwich flange (540, 640) of shank (520, 620) between cap (562, 662) and head (510, 610). More specifically, where cap (662) includes proximally facing projections (668), coupling cap (662) with head (610) includes inserting proximally facing projections (668) into recesses (658) of head (610). It is envisioned that coupling head (510, 610, 710) with shank (520, 620, 720) may include, for example, one or more overmolding, welds, adhesive, and/or mechanical securement features (e.g. projections (668)).

Those of ordinary skill in the art will understand that staples formed by anvil (400, 500, 600, 700) will have a three-dimensional profile, where the legs are angularly offset from a plane passing through a crown of the staple; in addition to being bent generally toward each other. By way of example only, the staples formed using anvil (400, 500, 600, 700) may have an appearance similar to at least some of the staples shown and described in U.S. Pub. No. 2014/0239037, entitled "Staple Forming Features for Surgical Stapling Instrument," published Aug. 28, 2014, now U.S. Pat. No. 10,092,292, issued on Oct. 9, 2018, the disclosure of which is incorporated by reference herein. By way of further example only, the staples formed using anvil (400, 500, 600, 700) may have an appearance similar to at least some of the staples shown and described in U.S. Pat. Pub. No. 2018/0132849, entitled "Staple Forming Pocket Configurations for Circular Surgical Stapler Anvil," published May 17, 2018, the disclosure of which is incorporated by reference herein. Additional features of anvils are disclosed in U.S. Pub. No. 2017/0258471 published Sep. 14, 2017; U.S. Pub. No. 2015/0083772 published Mar. 26, 2015, now abandoned; U.S. Pub. No. 2015/0083774 published Mar. 26, 2015, now U.S. Pat. No. 9,907,552, issued Mar. 6, 2018; U.S. Pub. No. 2016/0374672 published Dec. 29, 2016; U.S. Pub. No. 2018/0132853 published May 17, 2018; U.S. Pub. No. 2018/0132849 published May 17, 2018, U.S. patent application Ser. No. 15/581,640, entitled "Liquid-Immune Trigger Circuit for Surgical Instrument," filed Apr. 28, 2017, issued as U.S. Pat. No. 10,729,444 on Aug. 4, 2020, and U.S. patent application Ser. No. 15/581,546, entitled "Hysteresis Removal Feature in Surgical Stapling Instrument," filed Apr. 28, 2017, issued as U.S. Pat. No. 10,695,068 on Jun. 30, 2020, the disclosures of which are incorporated by reference herein.

In addition to or in lieu of the foregoing, anvil (400, 500, 600, 700) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing an anvil of a surgical circular stapler, wherein the anvil includes a head and a shank extending proximally from the head, the method comprising: (a) forming the head of a surgical circular stapler using a metal injection molding process; (b) forming an annular array of staple forming pockets in the head; (c) machining the shank of the surgical circular stapler; and (d) coupling together the head and the shank of the surgical circular stapler that were separately manufactured.

Example 2

The method of Example 1, further comprising: forming the shank using a metal injection molding process prior to machining the shank.

Example 3

The method of any one or more of Examples 1 through 2, further comprising: machining at least a portion of the head after forming the head using the metal injection molding process.

Example 4

The method of any one or more of Examples 1 through 2, wherein forming the head using the metal injection molding process and forming the annular array of staple forming pockets in the head are performed simultaneously.

Example 5

The method of any one or more of Examples 1 through 2, wherein forming the head using the metal injection molding process occurs before forming the annular array of staple forming pockets in the head.

Example 6

The method of any one or more of Examples 1 through 5, wherein after forming the annular array of staple forming pockets using the metal injection molding process, the method further comprises coining or electrochemical machining at least a portion of at least one staple forming pocket of the annular array of staple forming pockets.

Example 7

The method of Example 6, wherein the portion coined or electrochemically machined is both smoother and denser than another portion that was not coined or electrochemical machined.

Example 8

The method of any one or more of Examples 6 through 7, wherein the portion coined or electrochemically machined is a central portion of at least one staple forming pocket of the annular array of staple forming pockets.

Example 9

The method of any one or more of Examples 1 through 8, wherein the shank includes a flange extending radially outward from a distal end of the shank.

Example 10

The method of Example 9, wherein forming the head further comprises forming the head to include a distal outer surface and a distal recessed portion that is disposed proximal to the distal outer surface, wherein the distal recessed portion is sized and configured to receive the flange of the shank.

Example 11

The method of Example 10, wherein the flange includes opposing proximal and distal surfaces, wherein coupling the head with the shank further comprises contacting the proximal surface of the flange with the distal recessed portion of the head.

Example 12

The method of Example 11, wherein contacting the proximal surface of the flange with the distal recessed portion of the head further comprises contacting the proximal surface of the flange with the distal recessed portion of the head such that the distal outer surface of the head is generally flush with the distal surface of the flange.

Example 13

The method of any one or more of Examples 9 through 12, wherein the flange includes an inner shallow portion and a rounded outer edge portion, wherein coupling the head with the shank further comprises coupling a proximal surface of the flange with a distal surface of the head.

Example 14

The method of any one or more of Examples 9 through 13, wherein coupling the head with the shank further comprises coupling a cap with the head to sandwich the flange of the shank between the cap and the head.

Example 15

The method of Example 14, wherein the cap includes at least one proximally facing projection and the head includes at least one corresponding recess, wherein coupling the cap with the head further comprises inserting the at least one proximally facing projection into the at least one recess.

Example 16

A method of manufacturing an anvil of a surgical circular stapler, wherein the anvil includes a head and a shank extending proximally from the head, wherein the head includes an annular array of staple forming pockets, the method comprising: (a) forming the head including the annular array of staple forming pockets; (b) coining or electrochemical machining at least a portion of at least one staple forming pocket of the annular array of staple forming pockets; (c) machining the shank; and (d) coupling the head with the shank that were separately manufactured.

Example 17

The method of Example 16, wherein the portion coined or electrochemically machined is a central portion of the at least one staple forming pocket, wherein the central portion, once coined or electrochemically machined, is both smoother and denser than another portion that was not coined or electrochemical machined.

Example 18

The method of any one or more of Examples 16 through 17, further comprising: forming the shank using a metal injection molding process prior to machining the shank.

Example 19

A surgical instrument comprising: (a) a body; (b) a shaft extending distally from the body; (c) a stapling head assembly positioned at a distal end of the shaft, wherein the stapling head assembly includes: (i) an anvil coupling feature, (ii) at least one annular array of staples, and (iii) a staple driver, wherein the staple driver is operable to drive the at least one annular array of staples; and (d) an anvil, wherein the anvil is configured to couple with the anvil coupling feature, wherein the anvil is further configured to deform the staples driven by the staple driver, wherein the anvil comprises: (i) a shank, and (ii) a head configured to be coupled with the shank, wherein the head includes an annular array of staple forming pockets, wherein a portion of at least one staple forming pocket of the annular array of staple forming pockets has a smoother and denser surface than the remainder of the staple forming pocket.

Example 20

The surgical instrument of Example 19, wherein the portion is a central portion that is interposed between first and second outer portions, wherein the first and second outer portions have a rougher and less dense surface than the central portion of the staple forming pocket.

Example 21

A surgical instrument comprising: (a) a body; (b) a shaft extending distally from the body; (c) a stapling head assembly positioned at a distal end of the shaft, wherein the stapling head assembly includes: (i) an anvil coupling feature, (ii) at least one annular array of staples, and (iii) a staple driver, wherein the staple driver is operable to drive the at least one annular array of staples; and (d) an anvil, wherein the anvil is configured to couple with the anvil coupling feature, wherein the anvil is further configured to deform the staples driven by the staple driver, wherein the anvil comprises: (i) a shank, and (ii) a head configured to be coupled with the shank and formed using a metal injection molding process, wherein the head includes an annular array of staple forming pockets.

Example 22

The surgical instrument of Example 21, wherein the head is machined after being formed using the metal injection molding process.

Example 23

The surgical instrument of any one or more of Examples 21 through 22, wherein the head and the annular array of staple forming pocket are formed simultaneously during the metal injection molding process.

Example 24

The surgical instrument of any one or more of Examples 21 through 23, wherein a portion of the staple forming pocket is coined or electrochemical machined to produce the smoother and denser surface than the remainder of the staple forming pocket.

Example 25

The surgical instrument of Example 24, wherein the portion coined or electrochemically machined a central portion of at least one staple forming pocket of the annular array of staple forming pockets.

Example 26

The surgical instrument of any one or more of Examples 21 through 25, wherein the shank is formed using a metal injection molding process, wherein the shank includes a flange extending radially outward from a distal end of the shank.

Example 27

The surgical instrument of Example 26, wherein the head further comprises a distal outer surface and a distal recessed portion that is disposed proximal to the distal outer surface, wherein the distal recessed portion is sized and configured to receive the flange of the shank.

Example 28

The surgical instrument of Example 27, wherein the flange includes opposing proximal and distal surfaces, wherein the proximal surface of the flange is configured to contact the distal recessed portion of the head.

Example 29

The surgical instrument of Example 28, wherein the proximal surface of the flange is configured to contact the distal recessed portion of the head such that the distal outer surface of the head is generally flush with the distal surface of the flange.

Example 30

The surgical instrument of any one or more of Examples 26 through 28, wherein the flange includes an inner shallow portion and a rounded outer edge portion, wherein a proximal surface of the flange is coupled with a distal surface of the head.

Example 31

The surgical instrument of any one or more of Examples 26 through 29, wherein a cap is fixably coupled with the head to sandwich the flange of the shank between the cap and the head.

Example 32

The surgical instrument of Example 31, wherein the cap includes at least one proximally facing projection, wherein the head includes at least one corresponding recess, wherein the at least one proximally facing projection is configured to be inserted into the at least one recess.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may also be readily combined with one or more teachings of U.S. Pub. No. 2017/0258471, entitled "Methods and Systems for Performing Circular Stapling," published Sep. 14, 2017, the disclosure of which is incorporated by reference herein. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a shaft extending distally;
   (b) a stapling assembly operatively coupled with the shaft, wherein the stapling assembly includes:
      (i) an anvil coupling projection,
      (ii) at least one annular array of staples, and
      (iii) a staple driver; and
   (c) an anvil configured to couple with the anvil coupling projection, wherein the anvil is further configured to deform the staples driven by the staple driver, wherein the anvil comprises:
      (i) a shank having a free distal end,
      (ii) a head that includes an annular array of staple forming pockets, and
      (iii) a cap coupling the shank and the head of the anvil together, wherein the cap defines a distal-most end of the anvil and includes a proximal end that overlies and directly contacts each of the free distal end of the shank and a distal end of the head to thereby fix the head relative to the shank, wherein the cap extends laterally across a distal end surface of the head to an outer-most edge of the distal end surface.

2. The surgical instrument of claim 1, wherein the cap is configured to sandwich a portion of the shank between the cap and the head.

3. The surgical instrument of claim 1, wherein the cap is overmolded onto the shank and the head of the anvil.

4. The surgical instrument of claim 1, wherein the cap includes at least one proximally facing projection, wherein the head includes at least one recess, wherein the at least one proximally facing projection is configured to be inserted into the at least one recess to secure the cap to the shank.

5. The surgical instrument of claim 1, wherein only a predetermined surface of at least one staple forming pocket of the annular array of staple forming pockets has a smoother and denser surface than a remaining surface of the staple forming pocket that is less dense than the predetermined surface.

6. The surgical instrument of claim 1, wherein the free distal end of the shank includes a flange extending radially outward, wherein the cap is configured to sandwich the flange of the shank between the cap and the head.

7. The surgical instrument of claim 6, wherein the cap is fixably coupled with at least one of the flange of the shank or the head.

8. The surgical instrument of claim 6, wherein the head comprises a distal outer surface and a distal recessed portion that is disposed proximal to the distal outer surface, wherein the distal recessed portion is sized and configured to receive the flange of the shank.

9. The surgical instrument of claim 8, wherein the flange includes a proximal surface that is opposed from the distal surface, wherein the proximal surface of the flange is configured to contact the distal recessed portion of the head.

10. The surgical instrument of claim 9, wherein the cap is coupled with the distal surface of the flange and the distal outer surface of the head.

11. The surgical instrument of claim 9, wherein the proximal surface of the flange is configured to contact the distal recessed portion of the head such that the distal outer surface of the head is generally flush with the distal surface of the flange.

12. The surgical instrument of claim 6, wherein the flange includes an inner shallow portion and a rounded outer edge portion, wherein a proximal surface of the flange is coupled with a distal surface of the head.

13. The surgical instrument of claim 1, wherein the head is formed from a metallic material, wherein the shank is formed from a metallic material, and wherein the cap is formed from a polymeric material.

14. A surgical instrument comprising:
   (a) a shaft extending distally;
   (b) a stapling assembly positioned at a distal end of the shaft, wherein the stapling assembly includes:
      (i) an anvil coupling feature,
      (ii) at least one annular array of staples, and
      (iii) a staple driver, wherein the staple driver is operable to drive the at least one annular array of staples; and (c) an anvil configured to couple with the anvil coupling feature, wherein the anvil is further configured to deform the staples driven by the staple driver, wherein the anvil comprises:
 (i) a shank that includes a flange and defines an axial direction,
 (ii) a head that includes an annular array of staple forming pockets, wherein a distal surface of the flange is flush with a distal surface of the head, and
 (iii) a cap sandwiching the flange of the shank between the cap and the head of the anvil in the axial direction, wherein the cap is positioned distal to the distal surfaces of the head and the shank and is configured to couple the head to the shank.

15. The surgical instrument of claim 14, wherein the cap is overmolded onto the flange of the shank and the head of the anvil to sandwich the flange of the shank between the cap and the head of the anvil.

16. The surgical instrument of claim 14, wherein the head is formed from a metallic material, and wherein the shank is formed from a metallic material, wherein the cap is formed from a polymeric material.

17. A method of manufacturing an anvil of a surgical circular stapler, wherein the anvil includes a head and a shank extending proximally from the head, the method comprising:
 (a) manufacturing the head and the shank separately from one another;
 (b) aligning the shank with the head such that a distal surface of the shank is flush with a distal surface of the head; and
 (c) once the distal surface of the shank is flush with the distal surface of the head, coupling together the head and the shank of the anvil of the surgical circular stapler using at least one overmolding process.

18. The method of claim 17, wherein the shank includes a flange, wherein the overmolding process further comprises overmolding a cap onto at least one the head or the shank to sandwich a flange of the shank between the cap and the head.

19. The method of claim 17, wherein coupling together the head and the shank of the anvil further comprises overmolding the head directly to the shank of the anvil.

20. The method of claim 17, wherein manufacturing the head and the shank separately from one another further comprises:
 (a) forming the head using a metal injection molding process;
 (b) forming an annular array of staple forming pockets in the head; and
 (c) machining the shank of the surgical circular stapler.

\* \* \* \* \*